United States Patent [19]
Shirasaki et al.

[11] Patent Number: 5,522,395
[45] Date of Patent: Jun. 4, 1996

[54] ELECTRONIC SPHYGMOMANOMETER AND METHOD OF CONTROLLING OPERATION OF SAME

[75] Inventors: Osamu Shirasaki; Teruya Nishina; Yoshinori Miyawaki; Masashi Fukura, all of Kyoto, Japan

[73] Assignee: Omron Corporation, Kyoto, Japan

[21] Appl. No.: 492,947

[22] Filed: Jun. 21, 1995

Related U.S. Application Data

[63] Continuation of Ser. No. 140,066, Oct. 28, 1993, abandoned.

[30] Foreign Application Priority Data

May 1, 1991 [JP] Japan .................. 3-099919

[51] Int. Cl.$^6$ .................. A61B 5/0225
[52] U.S. Cl. .................. 128/682; 128/681
[58] Field of Search .................. 128/677–686, 128/672; 364/412.03

[56] References Cited

U.S. PATENT DOCUMENTS

| | | | |
|---|---|---|---|
| 4,417,587 | 11/1983 | Ichinomiya et al. | 128/682 |
| 4,461,266 | 7/1984 | Hood, Jr. et al. | 128/681 |
| 4,660,567 | 4/1987 | Kaneko et al. | 128/682 |
| 4,872,461 | 10/1989 | Miyawaki | 128/682 X |
| 5,197,478 | 3/1993 | Souma | 128/682 X |
| 5,261,414 | 11/1993 | Aung et al. | 128/683 |
| 5,316,006 | 5/1994 | Inage et al. | 128/680 X |
| 5,323,782 | 6/1994 | Shirasaki et al. | 128/680 |
| 5,335,665 | 8/1994 | Suzuki | 128/680 |

FOREIGN PATENT DOCUMENTS

| | | |
|---|---|---|
| 249990 | 12/1987 | European Pat. Off. . |
| 249243 | 12/1987 | European Pat. Off. . |
| 2488793 | 2/1982 | France . |
| 2593380 | 7/1987 | France . |
| 61-130202 | 8/1986 | Japan . |
| 62-14832 | 1/1987 | Japan . |
| 62-47337 | 3/1987 | Japan . |
| 63-130043 | 6/1988 | Japan . |
| 63-277035 | 11/1988 | Japan . |
| 1-101967 | 4/1989 | Japan . |
| 1-256930 | 10/1989 | Japan . |

*Primary Examiner*—Angela D. Sykes
*Assistant Examiner*—Stephen Huang
*Attorney, Agent, or Firm*—Fish & Richardson

[57] ABSTRACT

The amplitude of a pulse wave that appears in a form superimposed upon cuff pressure is detected every beat of a heartbeat in synchronism with the beat not only in the course of depressurization but also in the course of pressurization. The maximum value Amaxi of the pulse-wave amplitude in the course of pressurization is multiplied by a prescribed coefficient to decide a threshold value TH. The threshold value TH is calculated as a value equivalent to a pulse-wave amplitude corresponding to systolic pressure that would be determined in the course of depressurization. After the cuff is pressurized to the target pressure, a transition is made to the depressurizing process. It is judged that cuff pressurization is inadequate if the initial pulse-wave amplitude in the course of depressurization is greater than the threshold value TH. Thus, whether or not cuff pressurization is inadequate can be judged appropriately at all times without any influence due to personal differences or physical condition.

9 Claims, 8 Drawing Sheets

Fig. 3

| PULSE-WAVE NUMBER (n) | PULSE-WAVE AMPLITUDE Amp(n) | CUFF PRESSURE Pc(n) |
|---|---|---|
| 1 | | |
| 2 | | |
| 3 | | |
| 4 | | |
| 5 | | |
| 6 | | |
| ..... | ..... | ..... |

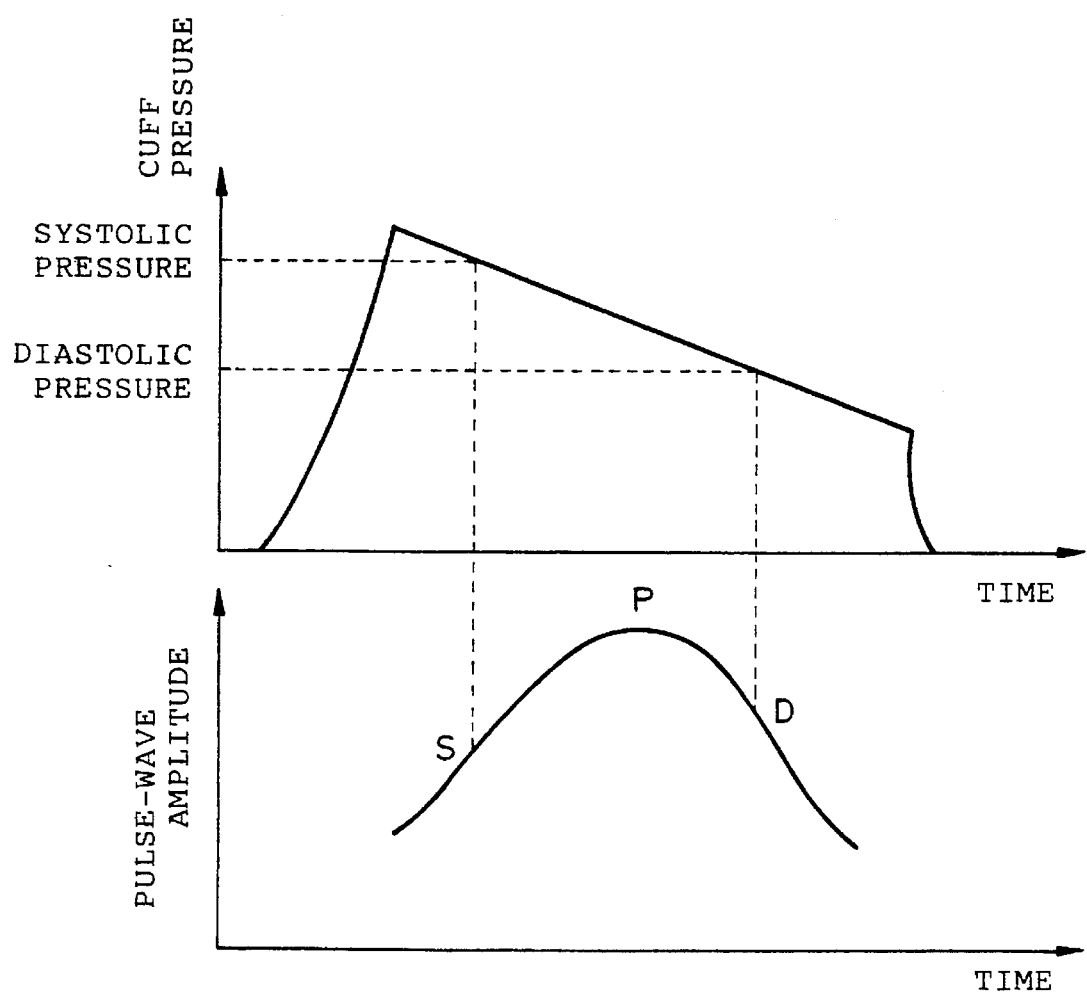

# ELECTRONIC SPHYGMOMANOMETER AND METHOD OF CONTROLLING OPERATION OF SAME

This application is a continuation of U.S. application Ser. No. 08/140,066, filed Oct. 28, 1993, now abandoned.

TECHNICAL FIELD

This invention relates to an oscillometric-type electronic sphygmomanometer and a method of controlling the operation thereof.

DESCRIPTION OF THE RELATED ART

In an oscillometric-type electronic sphygmomanometer, the pressure in a cuff (an arm band, a rubber bag or a manshette) for applying pressure to part of a living body (the cuff generally is wound around an upper arm of the human body) is elevated to a pressure above maximum blood pressure (systolic pressure SP), after which the cuff is gradually depressurized. During the depressurizing process, a fluctuation in pressure that appears in a form superimposed on the cuff pressure in synchronism with the heartbeat is captured as a pulse wave. The values of blood pressure (the maximum and minimum blood pressures) are determined by observing a change in the amplitude of the pulse wave.

FIG. 8 illustrates a change in cuff pressure and a change in the amplitude of the pulse wave with time in a process for measuring blood pressure. Though the fluctuation in pressure synchronized to the heartbeat is superimposed upon the cuff pressure, as mentioned above, the graph of cuff pressure in FIG. 8 is drawn without showing this fluctuation in pressure. The graph of the amplitude of the pulse wave is an envelope, on the time axis, of the waveform of this fluctuation in pressure.

After the cuff pressure is raised above systolic pressure (maximum blood pressure), the cuff is gradually depressurized. When the cuff pressure falls below diastolic pressure (minimum blood pressure), the cuff is depressurized at a rapid rate (i.e., the air is discharged at a rapid rate). The amplitude of the pulse wave is small when the cuff pressure is higher than the systolic pressure (maximum blood pressure), increases as the cuff is depressurized and attains its maximum value slightly before the cuff pressure becomes equal to diastolic pressure (minimum blood pressure) (cuff pressure at this time is approximately equal to average blood pressure). If cuff pressure is reduced further, the amplitude of the pulse wave also decreases. In the graph of the envelope of pulse-wave amplitude, S represents a position corresponding to systolic pressure, D a position corresponding to diastolic pressure and P the point at which the pulse wave peaks.

In the oscillometric method, the systolic and diastolic pressures are found by using the peak point P to determine the S and D points corresponding respectively to systolic pressure and diastolic pressure on the envelope of the pulse-wave amplitude. More specifically, the S and D points are determined as points at which the amplitude of the pulse wave is a predetermined percentage of the maximum value (the P point). For example, the S point is calculated as the point at which the amplitude of the pulse wave is 50% of the maximum amplitude value, and the D point is calculated as the point at which the amplitude of the pulse wave is 70% of the maximum amplitude value.

Since cuff pressure first is raised to a predetermined pressure value and then is gradually reduced, the amplitude of the pulse wave passes through the S point, P point and D point in the order mentioned. In accordance with the above-described method of deciding the S point, the S point cannot be sensed until the P point is traversed. Accordingly, if the pressure applied to the cuff has not attained a cuff pressure corresponding to the S point, the cuff pressure corresponding to the amplitude of the pulse wave at the S point is unknown and therefore it is impossible to measure the maximum blood pressure. This represents inadequate pressurization. However, since inadequate pressurization is ascertained at the moment the P point is detected, the fact that pressurization is inadequate (i.e., the fact that measurement of maximum blood pressure is not possible) is not known until this time. In general, since average blood pressure (which substantially corresponds to the P point, as mentioned above) is fairly close to minimum blood pressure, the fact that measurement of maximum blood pressure is impossible cannot be ascertained until just prior to the end of measurement of blood pressure.

For this reason, it is required that the user of the oscillometric sphygmomanometer estimate the maximum blood pressure when pressurizing the cuff and set a pressure sufficiently higher than the maximum blood pressure as the pressurization target value. However, this is difficult in the case of an ordinary user or a hypertensive individual, whose blood pressure tends to fluctuate, and the fact is that inadequate pressurization frequently occurs. Moreover, since the inadequacy in pressurization is not ascertained until just before the end of measurement of blood pressure, essentially the measurement of blood pressure must be performed again. A problem which arises is that this has an effect upon the operability and rapidity of the measurement of blood pressure and even upon measurement accuracy.

In order to solve this problem, there have been proposed a method (apparatus) in which, after the cuff is pressurized, the amplitude of the initial pulse wave detected at the moment of the transition to the depressurization process is compared with a preset reference value and pressurization is judged to be inadequate when the amplitude of the pulse wave is greater than the reference value (see Japanese Utility Model Laid-Open No. 61-130202), and a method (apparatus) in which a threshold value is set based upon the cuff pressure that prevails at the end of cuff pressurization, the amplitude of the pulse wave first detected at the start of depressurization is compared with the set threshold value and pressurization is judged to be inadequate when the amplitude of the pulse wave is greater than the threshold value (see Japanese Patent Application Laid-Open No. 62-47337).

In the former method, however, the reference value is fixed within the sphygmomanometer in advance, and absolutely no consideration is given to the fact that there is a difference in the amplitude of the pulse wave from one individual to another. Consequently, the judgment as to whether pressurization is inadequate is not always correct.

The latter method utilizes the fact that there is a proportional correlation between the maximum value of blood pressure and the amplitude of the pulse wave. The threshold value is set at the end of cuff pressurization, namely on the basis of the pressurization target value; the larger the pressurization target value, the higher the threshold value is made. Accordingly, a relatively high threshold value is set for a hypertensive individual having a large pulse-wave amplitude, and a relatively low threshold value is set for a hypotensive individual having a small pulse-wave amplitude. Thus, a difference among individuals in terms of the amplitude of the pulse wave is taken into account. However, since the pressurization target value of cuff pressure is set by the user, the target value is not always set correctly. The value of maximum blood pressure not only differs among individuals but also varies depending upon the physical condition of one and the same individual at the time blood pressure is measured. The pressurization target value must be set so as to appropriately reflect such a variation in the value of maximum blood pressure. Unless the pressurization target value is set appropriately, there is the danger that the judgment as to whether pressurization is inadequate may be erroneous.

DISCLOSURE OF THE INVENTION

The present invention provides an electronic sphygmomanometer, as well as a method of controlling the operation thereof, in which the fact that the amplitude of the pulse wave varies in dependence upon individual differences and physical condition is taken into consideration so that an inadequacy in pressurization can be judged correctly at all times.

The present invention provides an electronic sphygmomanometer having pressurizing means for pressurizing a cuff to a prescribed target pressure value, depressurizing means for gradually depressurizing the cuff after the cuff is pressurized to the prescribed target pressure value by the pressurizing means, pressure detecting means for detecting fluid pressure within the cuff, pulse-wave extracting means for extracting, from a cuff pressure signal obtained from the pressure detecting means, a heartbeat-synchronized pulse-wave component signal superimposed upon the cuff pressure signal, pulse-wave amplitude detecting means for detecting amplitude of a pulse wave extracted by the pulse-wave extracting means every heartbeat, and blood-pressure determining means for determining a value of blood pressure based upon an amplitude signal from the pulse-wave amplitude detecting means and a pressure signal from the pressure detecting means in the course of cuff depressurization by the depressurizing. The electronic sphygmomanometer has maximum pulse-wave amplitude detecting means for detecting a maximum value of pulse-wave amplitudes obtained from the pulse-wave amplitude detecting means in the course of cuff pressurization by the pressurizing means, threshold-value deciding means for deciding a threshold value based upon the maximum value of pulse-wave amplitude detected by the maximum pulse-wave amplitude detecting means, and cuff pressurization-inadequacy judging means for comparing the pulse-wave amplitude obtained from the pulse-wave amplitude detecting means at a time early in the course of cuff depressurization by the depressurizing means with the threshold value decided by the threshold-value deciding means, and judging that cuff pressurization is inadequate in a case where the pulse-wave amplitude is greater than the threshold value.

The present invention provides a method of controlling the operation of an electronic sphygmomanometer in which a cuff is pressurized to a prescribed target pressure value and then gradually depressurized, pressure within the cuff is detected and the amplitude of a heartbeat-synchronized pulse-wave component superimposed upon cuff pressure is detected for every heartbeat in the course of cuff depressurization, and a value of blood pressure is determined based upon cuff pressure and pulse-wave amplitude detected in the course of cuff depressurization. The method includes detecting the amplitude of the pulse-wave component of every heartbeat and detecting a maximum value of the detected pulse-wave amplitudes in the course of pressurization for pressurizing the cuff to the prescribed target pressure value, deciding a threshold value based upon the maximum value of pulse-wave amplitude detected, comparing the pulse-wave amplitude obtained at a time early in the course of cuff depressurization, which begins after the cuff is pressurized to the prescribed target pressure value, with the threshold value, and judging that cuff pressurization is inadequate in a case where the pulse-wave amplitude is greater than the threshold value.

When it has been determined that cuff pressurization is inadequate, a new target pressure value greater than the above-mentioned prescribed target pressure value is set, depressurization of the cuff is suspended and the cuff is pressurized again up to the new target pressure value. When it has been determined that cuff pressurization is not inadequate, namely that cuff pressurization is adequate, the depressurization processing continues and measurement of blood pressure proceeds.

The above-mentioned threshold value is decided as a value equivalent to a pulse-wave amplitude corresponding to systolic pressure (maximum blood pressure) that would be determined at setting of blood pressure in the course of depressurization.

In accordance with the present invention, the pulse-wave amplitude of the individual undergoing measurement is actually detected in the course of pressurization, and the threshold value for the purpose of judging pressurization inadequacy is decided based upon the maximum pulse-wave amplitude prevailing in the course of pressurization. Accordingly, whether or not pressurization is inadequate can be ascertained under conditions exactly the same as those that prevail during measurement of blood pressure. In other words, according to the present invention, even if the amplitude of the pulse wave changes depending upon individual differences or physical condition, the threshold value is decided based upon the actual pulse-wave amplitude that has undergone the change. This makes it possible to judge pressurization inadequacy correctly at all times.

BRIEF DESCRIPTION OF THE DRAWINGS

FIG. 3 illustrates a table storing measured or calculated pulse-wave amplitudes and cuff pressures;

FIG. 8 is a graph for describing a concept for measuring blood pressure in an oscillometric sphygmomanometer.

BEST MODE FOR CARRYING OUT THE INVENTION

Figure 1:
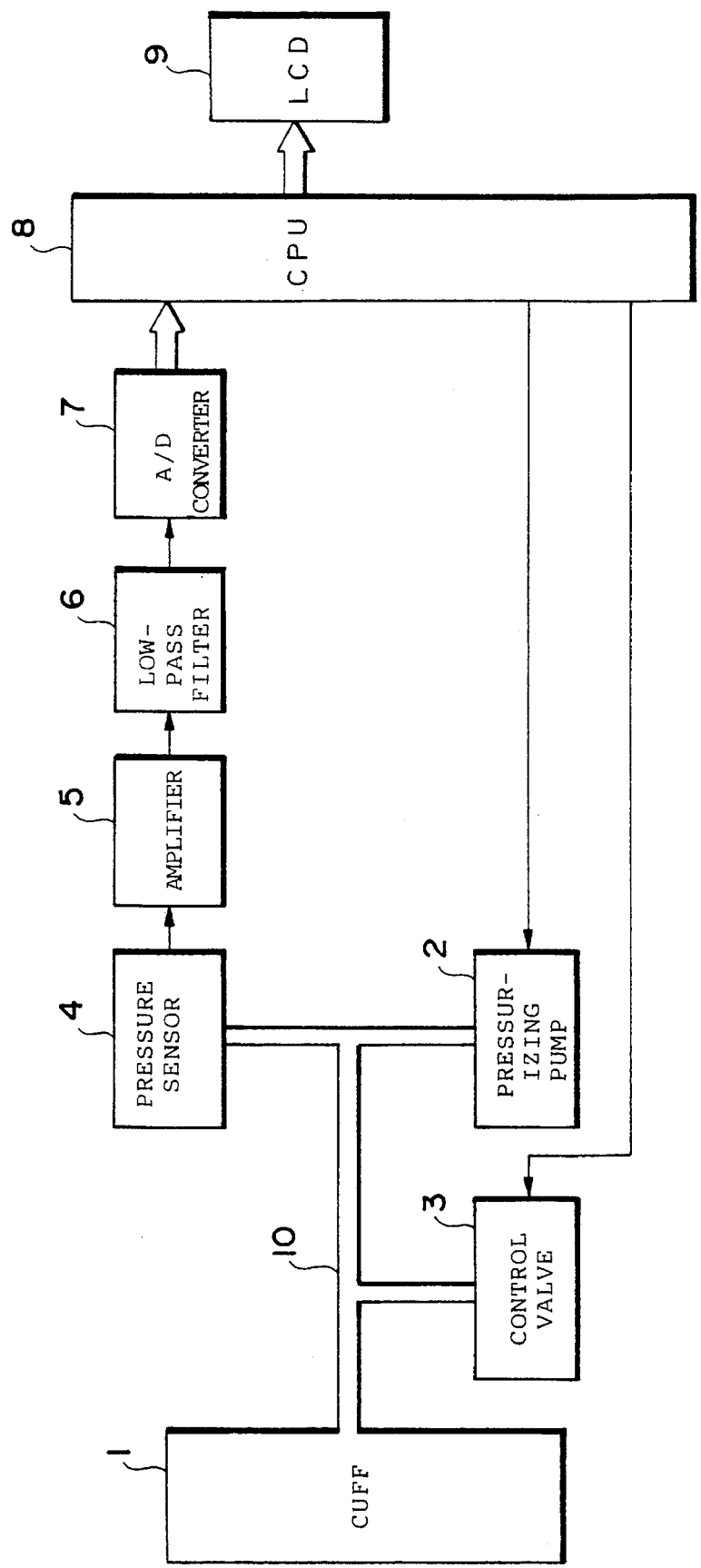
FIG. 1 is a block diagram illustrating the electrical configuration of an electronic sphygmomanometer.

FIG. 1 is a block diagram illustrating the electrical configuration of an embodiment of an electronic sphygmomanometer according to the present invention.

The pneumatic system of the electronic sphygmomanometer is composed of a cuff 1, a pressurizing pump 2 for feeding air into the cuff 1 to pressurize the same, and a control valve (a combination of a rapid-discharge valve and a slow-speed discharge valve) 3 for reducing the pressure within the cuff by discharging the air within the cuff 1. These components are connected via air tubing 10. The pressurizing pump 2 and control valve 3 are electrically connected to, and are controlled by, a CPU 8, described later.

A pressure sensor 4 is provided within the air tubing 10. The pressure sensor 4 is realized by, for example, a diaphragm converter using a strain gauge, a semiconductor pressure transducer, etc. An output analog signal from the pressure sensor 4 is amplified by an amplifier 5 and then applied to an A/D converter 7 via a low-pass filter 6. This signal is converted into digital data in the A/D converter 7. The low-pass filter 6 is for eliminating pressure noise which is produced by the pressurizing pump 2 and becomes mixed in the cuff-pressure signal. The filter is especially useful when a pulse wave is detected in the course of pressurization. The noise-filtered digital data representing the detection output of the pressure sensor 4 is accepted by the CPU 8 at a fixed period.

The CPU 8 has a pulse-wave extracting function (a function for extracting data, which represents a pulse wave, from the cuff-pressure data), a pulse-wave amplitude calculating function [a function for recognizing starting and end points of a pulse wave for every heartbeat and for calculating the amplitude (peak value) of the pulse wave], and a blood-pressure calculating function (a function for calculating maximum and minimum values of blood pressure based upon a plurality of pulse-wave amplitudes obtained, namely an envelope of pulse waves). Further, the CPU 8 has a function for calculating a threshold value based upon the maximum pulse-wave amplitude obtained from cuff pressure in the course of pressurization (the threshold value is a value for judging whether cuff pressurization is inadequate; in this embodiment, the threshold value is calculated as 50% of a maximum value Amax of the pulse-wave amplitude), and a cuff-pressurization inadequacy detecting function for comparing the pulse-wave amplitude that prevails immediately after the transition to the cuff-depressurization process (i.e., that prevails at the first heartbeat that follows the end of cuff pressurization) with the threshold value, judging that pressurization is adequate if the pulse-wave amplitude at the first heartbeat is less than the threshold value, and judging that pressurization is inadequate (i.e., that there is no data for deciding maximum blood pressure) if the pulse-wave amplitude at the first heartbeat is greater than the threshold value. If it is judged that cuff pressurization is inadequate, the CPU 8 re-pressurizes (provides addition pressurization to) the cuff automatically. Furthermore, the CPU 8 causes the maximum and minimum values of blood pressure determined to be displayed on a liquid-crystal display unit 9.

Figure 2:
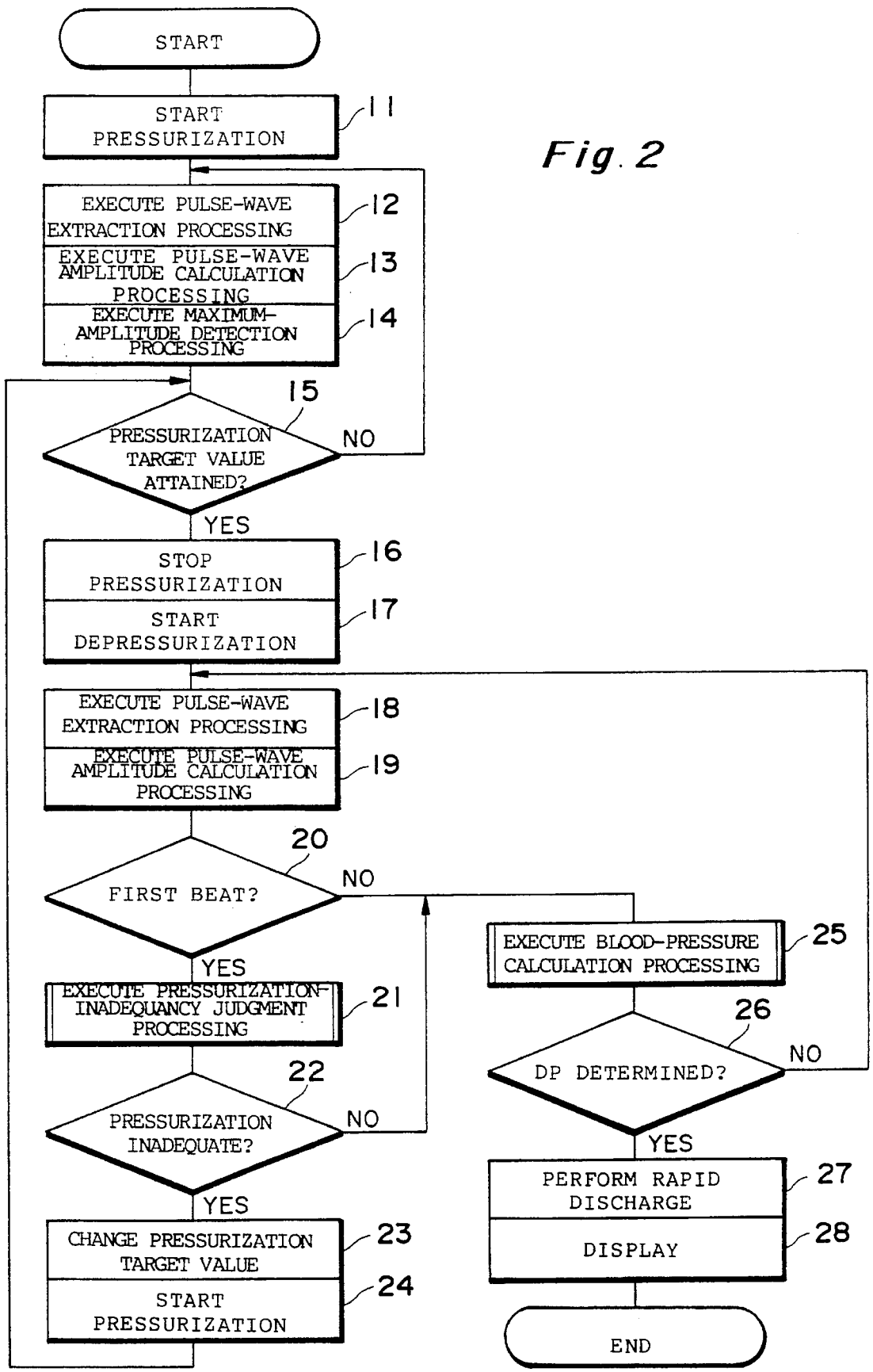
FIG. 2 is a flowchart illustrating the entirety of blood-pressure measurement processing in the electronic sphygmomanometer.

FIG. 2 is a flowchart showing the specific processing operation of the electronic sphygmomanometer. This processing is executed primarily by the CPU 8.

When a power-supply switch and pressurizing switch are turned on, pressurization of the cuff 1 starts (step 11). More specifically, the control valve 3 is closed and the pressurizing pump 2 is driven into operation. A pressurization target value is in advance by the user employing a manual switch.

An output signal from the pressure sensor 4 representing cuff pressure is accepted by the CPU 8 as digital data at a fixed period (sampling period) even during the course of pressurization. The sampling period is sufficiently smaller than the period of the pulse wave. Pulse-wave component data is extracted from the cuff-pressure data obtained in the course of pressurization (step 12). This is realized by a high-pass filter function implemented by a program. If the cut-off frequency of the high-pass filter is set to 0.7 Hz, then the transient response time at the start of pressurization can be held to about one second and recognition of the pulse wave can be started more rapidly. The amplitude of the pulse wave for every heartbeat is calculated based upon the pulse-wave component data thus obtained (step 13). From among the pulse waves captured during pressurization, the pulse wave having the maximum amplitude is identified and the value of this amplitude is stored in memory (step 14). More specifically, whenever the pulse-wave amplitude of one heartbeat is obtained, the value of this amplitude and the value of the maximum amplitude stored are compared. If the currently prevailing amplitude value is greater than the maximum amplitude value that prevailed up to the immediately preceding cycle, then the currently prevailing amplitude value is stored as the maximum amplitude value, thereby updating the maximum amplitude value.

The processing of steps 12–14 is executed with the pulse wave of one heartbeat serving as the unit of execution. This processing is followed by judging whether cuff pressure has attained the preset pressurization target value (step 15). If cuff pressure has not attained the pressurization target value, then the program returns to step 12. The processing of steps 12–14 is repeated until cuff pressure attains the pressurization target value.

When cuff pressure attains the pressurization target value, pressurization is halted (suspension of pressurizing-pump drive at step 16) and, at the same time, slow discharge is started (opening of slow-discharge valve at step 17) to make a transition to the measurement of blood pressure.

Processing (step 18) for extracting pulse-wave component data and processing (step 19) for calculating pulse-wave amplitude using the pulse-wave component data obtained is executed even in the course of slow discharge (depressurization) just as in the case of the pressurizing process described above.

When the above-described processing regarding the pulse wave of one beat ends, a check is made to determine whether the pulse wave that is the object of processing is that of the first beat that follows the start of depressurization (step 20). If the pulse wave is that of the first beat, then the program performs to processing for judging cuff pressurization inadequacy (step 21). The processing for judging cuff pressurization inadequacy will be described later in greater detail.

When it is judged in processing for judging cuff pressurization inadequacy that pressurization is inadequate (YES at step 22), the pressurization target value is changed (step 23). A value obtained by adding a prescribed pressure value (30 mmHg, for example) to the initial pressurization target value is set as the new pressurization target value. Next, depressurization is halted and pressurization is started again (step 24). The program then returns to step 15 so that pressurization up to the new pressurization target value is executed. An arrangement may be adopted in which the program returns from step 24 to step 12 so that processing for detecting maximum amplitude in the course of pressurization may be carried out.

The program proceeds to processing for calculating blood pressure (step 25) in a case where the heartbeat is not the first heartbeat following the start of depressurization (NO at step 20) and also in a case where pressurization is not inadequate (NO at step 22) even when the beat is the first heartbeat. The details of processing for calculating blood pressure also will be described later.

The processing of steps 18, 19 and 25 is repeated whenever one beat of a pulse wave is detected. Whenever one beat of a pulse wave is detected in the processing of steps 18 and 19, the number n of the pulse wave (the number is incremented in the order of appearance of the pulse waves starting from the moment the transition is made to the depressurizing process), the pulse-wave amplitude Amp(n) detected and cuff pressure Pc(n) prevailing at such time (this is the value obtained from the pressure sensor 4 and preferably has been rendered free of pulse-wave components) are stored in the form of a table in the memory of CPU 8, as illustrated in FIG. 3. The processing for calculating blood pressure is executed using this table.

When diastolic pressure (minimum blood pressure) (DP) is determined in blood-pressure calculation processing (YES at step 26), the program departs from repeated execution of steps 18, 19 and 25 and rapid discharge is carried out (opening of rapid-discharge valve) (step 27). The values of maximum and minimum blood pressure determined in the blood-pressure calculation processing are displayed on the display unit 9 (step 28).

Figure 4:
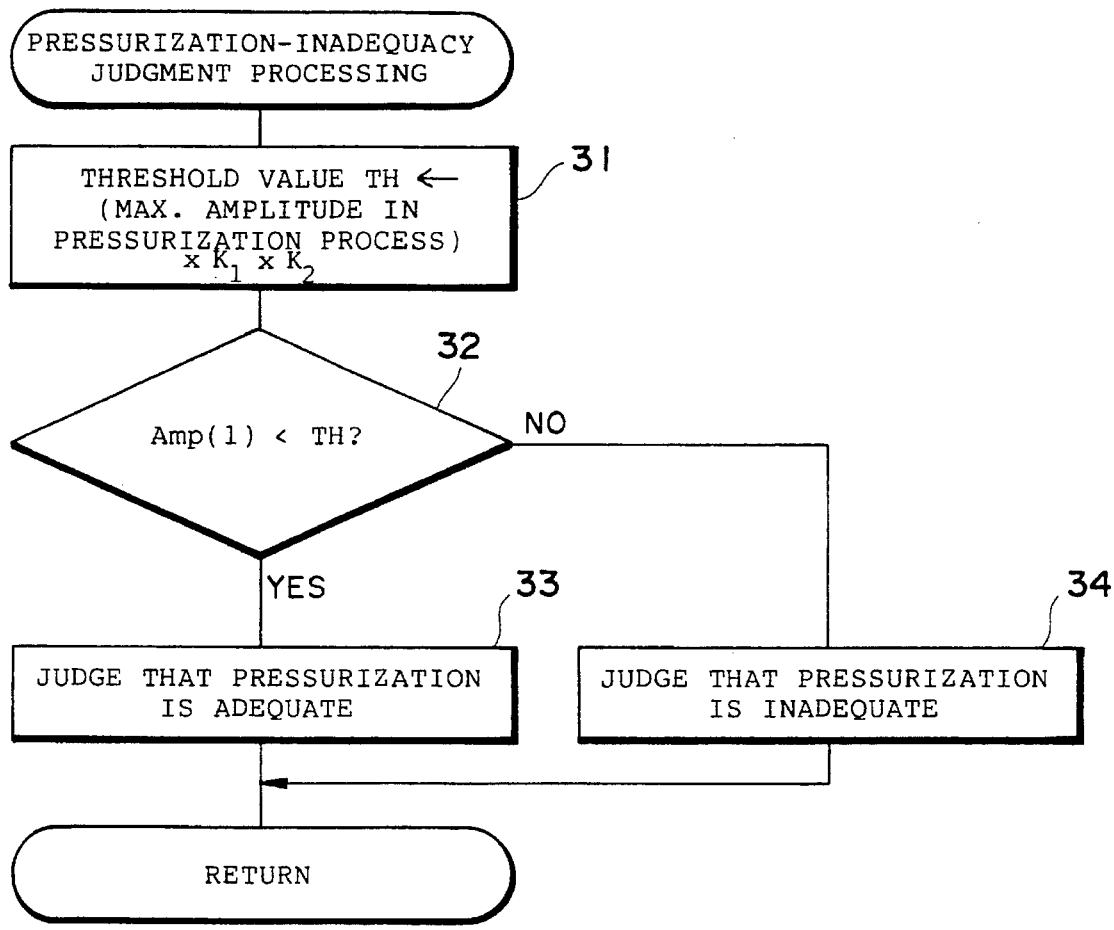
FIG. 4 is a flowchart illustrating the details of processing for judging pressurization inadequacy.

FIG. 4 illustrates the details of processing (step 21 in FIG. 2) for judging pressurization inadequacy.

A threshold value TH for judging cuff pressurization inadequacy is calculated (step 31). By way of example, the threshold value TH is calculated by multiplying the maximum pulse-wave amplitude, which has been detected in the pressurization process, by two coefficients $K_1$ and $K_2$.

$$\text{Threshold Value TH}=(\text{maximum pulse-wave amplitude in pressurization process})\times K_1 \times K_2 \tag{1}$$

Here $K_1$ is a coefficient dependent upon the characteristics of a filter for extracting a pulse-wave component. The filter for performing pulse-wave extraction in the course of pressurization may be the same as that used for measuring blood pressure in the course of depressurization (in which case the coefficient $K_1$ will be 1). In general, however, a transient response is produced in the filter output for several seconds following the start of pressurization, thereby hampering detection of the pulse wave. Accordingly, in order that the transient-response time may be shortened, it is preferred to make use of a filter having a higher cut-off frequency. In such case, since comparatively low-frequency components of the pulse wave also are eliminated, the amplitude of the pulse wave is compressed at a substantially constant rate. The maximum pulse-wave amplitude is multiplied by $K_1$ in order to correct for this.

The coefficient $K_2$, on the other hand, is the ratio (assumed here to be 0.5) of pulse-wave amplitude to maximum pulse-wave amplitude for the purpose of calculating systolic pressure (maximum blood pressure).

Figure 5:
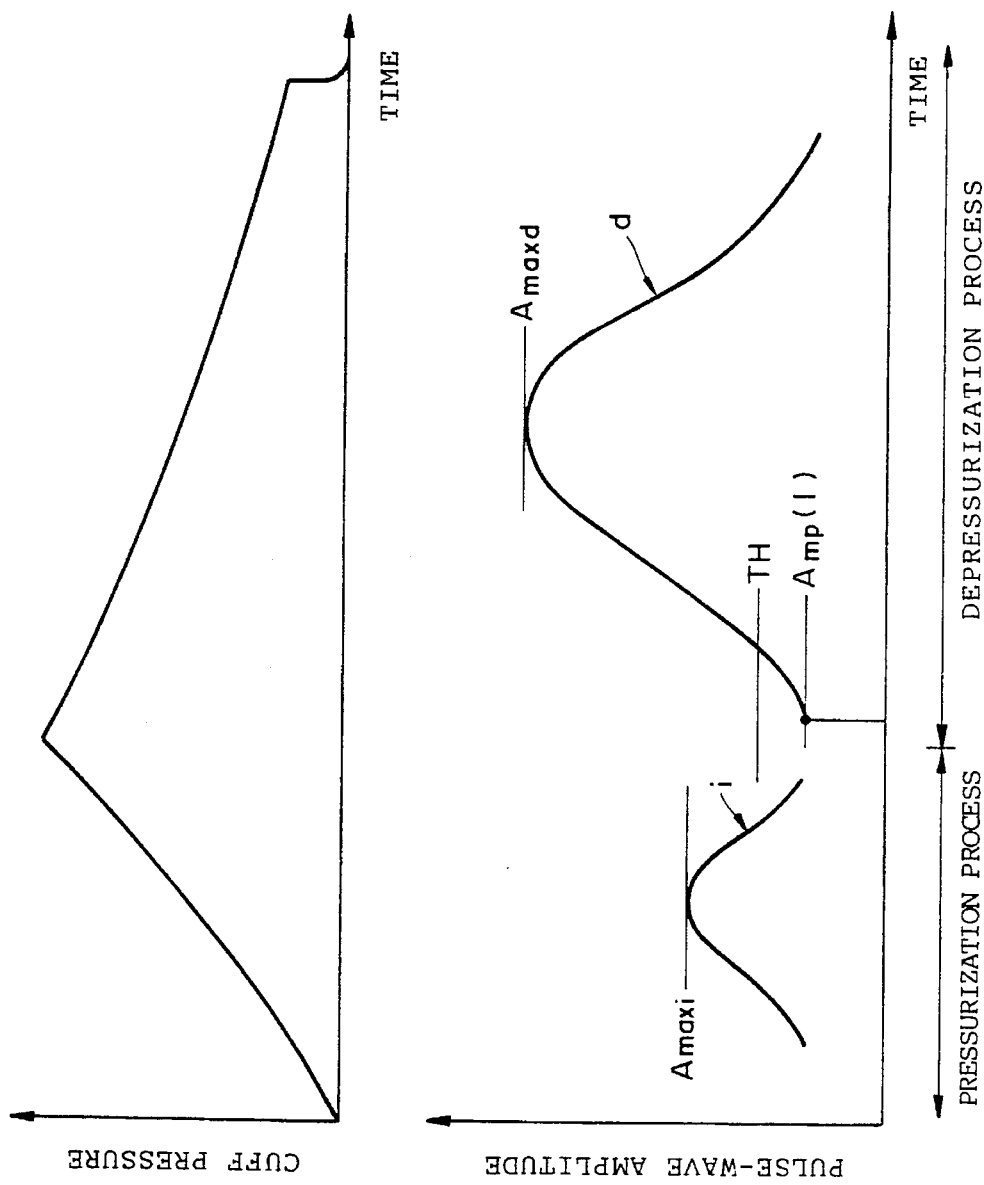
FIG. 5 is a graph showing changes in cuff pressure and pulse-wave amplitude in pressurization and depressurization processes.

The method of deciding the coefficient $K_1$ will now be described. FIG. 5 illustrates a pulse-wave amplitude envelope d in the course of depressurization and a pulse-wave amplitude envelope i in the course of pressurization. Maximum pulse-wave amplitude Amaxi in the course of pressurization is smaller, by a certain ratio, than the maximum pulse-wave amplitude Amaxd in the course of depressurization for the reason set forth earlier. The reciprocal of this ratio is the coefficient $K_1$. This ratio can be determined from a large number of examples of measurement of the kind shown in FIG. 6.

Figure 6:
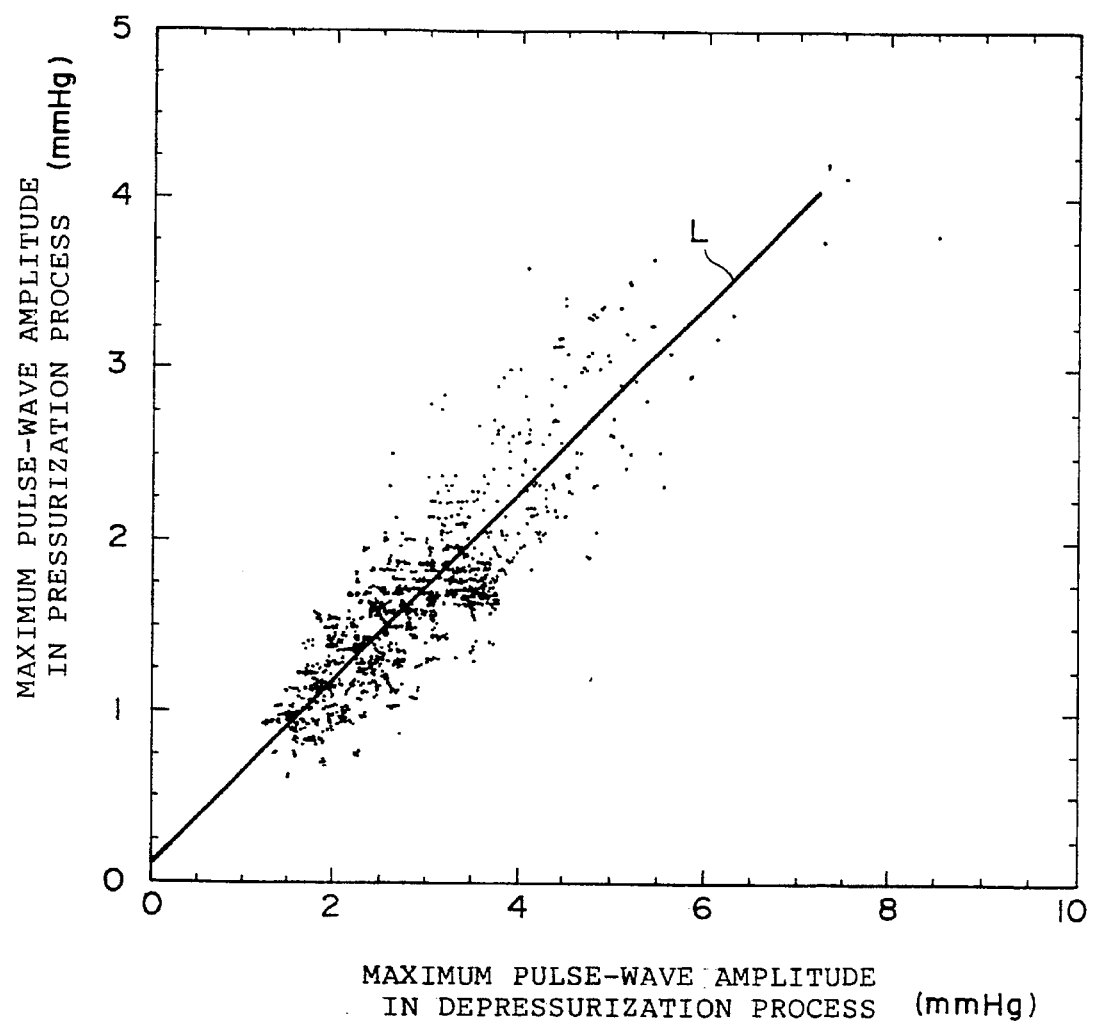
FIG. 6 is a correlation graph in which a large number of examples of measurement are plotted with regard to the relationship between maximum pulse-wave amplitude in the course of depressurization and maximum pulse-wave amplitude in the course of pressurization.

FIG. 6 is a plot of 599 measured points taking the maximum pulse-wave amplitude Amaxd in the course of depressurization along the horizontal axis and the maximum pulse-wave amplitude Amaxi in the course of pressurization along the vertical axis. A linear functional correlation exists between the maximum pulse-wave amplitude in the course of depressurization and the maximum pulse-wave amplitude in the course of pressurization. Let L represent this linear correlation. Further, if we let x represent the maximum pulse-wave amplitude in the course of depressurization, let y represent the maximum pulse-wave amplitude in the course of pressurization and assume roughly that the straight line L passes through the origin, then these will be related by the expression y=ax. In the examples of measurement shown in FIG. 6, we have approximately a =⅔. Accordingly, in a sphygmomanometer based on the examples of measurement illustrated in FIG. 6, the setting made is $K_1=1.5$.

In accordance with the above-described example, therefore, the threshold value TH of Equation (1) is expressed as follows:

$$\text{Threshold Value TH}=\text{Amaxi}\times 1.5\times 0.5 \tag{2}$$

It is judged whether the amplitude of the pulse wave [the amplitude of the pulse wave of the first heartbeat in the processing shown in FIG. 2; let this amplitude be represented by Amp (1)] immediately after the start of blood-pressure measurement, i.e., immediately after the transition to the depressurization process, is less than the above-mentioned threshold value TH (step 32).

If Amp(1) is greater than the threshold value TH, this means that cuff pressure is lower than the maximum blood pressure (the cuff pressure corresponding to the S point in FIG. 8). In other words, it is judged that pressurization is inadequate (step 34). If Amp(1) is smaller than the threshold value TH, then measurement of maximum blood pressure is possible and it is judged that pressurization is adequate (step 33).

Strictly speaking, the straight line L in the graph of FIG. 6 intersects the Y axis and therefore the straight line L is represented by y=ax+b. When this is taken into account, the threshold value may be calculated more correctly using the following equation:

$$\text{Threshold Value}=|\text{Amaxi}\times K_3+K_4|\times K_2 \tag{3}$$

It goes without saying that the judgment concerning pressurization inadequacy may be rendered using this threshold value TH.

When the threshold value TH is obtained in concrete terms using the examples of measurement shown in FIG. 6, we have the following:

The straight line L found from the examples of measurement of FIG. 6 is expressed by the following equation:

$$y=ax+b=0.5321x+0.1965 \tag{4}$$

This is expressed as follows when Amaxi, Amaxd are used:

$$\text{Amaxi}=a\cdot\text{Amaxd}+b \tag{5}$$

Solving Equation (5) with regard to Amaxd gives us $$\text{Amaxd}=(1/a)\text{Amaxi}-(b/a) \tag{6}$$

On the other hand, the threshold value TH is given by the following equation:

$$\text{Threshold Value TH} = (\text{maximum pulse-wave amplitude Amaxd in depressurization process}) \times K_2 \quad (7)$$

Therefore, substituting Equation (6) into Equation (7) gives us $$\text{Threshold value TH} = [(1/a)\text{Amaxi} - (b/a)] \times K_2 = (K_3 \cdot \text{Amaxi} - K_4) \times K_2 \quad (8)$$

where $$K_3 = 1/a = 1/0.5321 = 1.88 \quad (9)$$

$$K_4 = b/a = 0.1965/0.5321 = 0.37 \quad (10)$$

Figure 7:
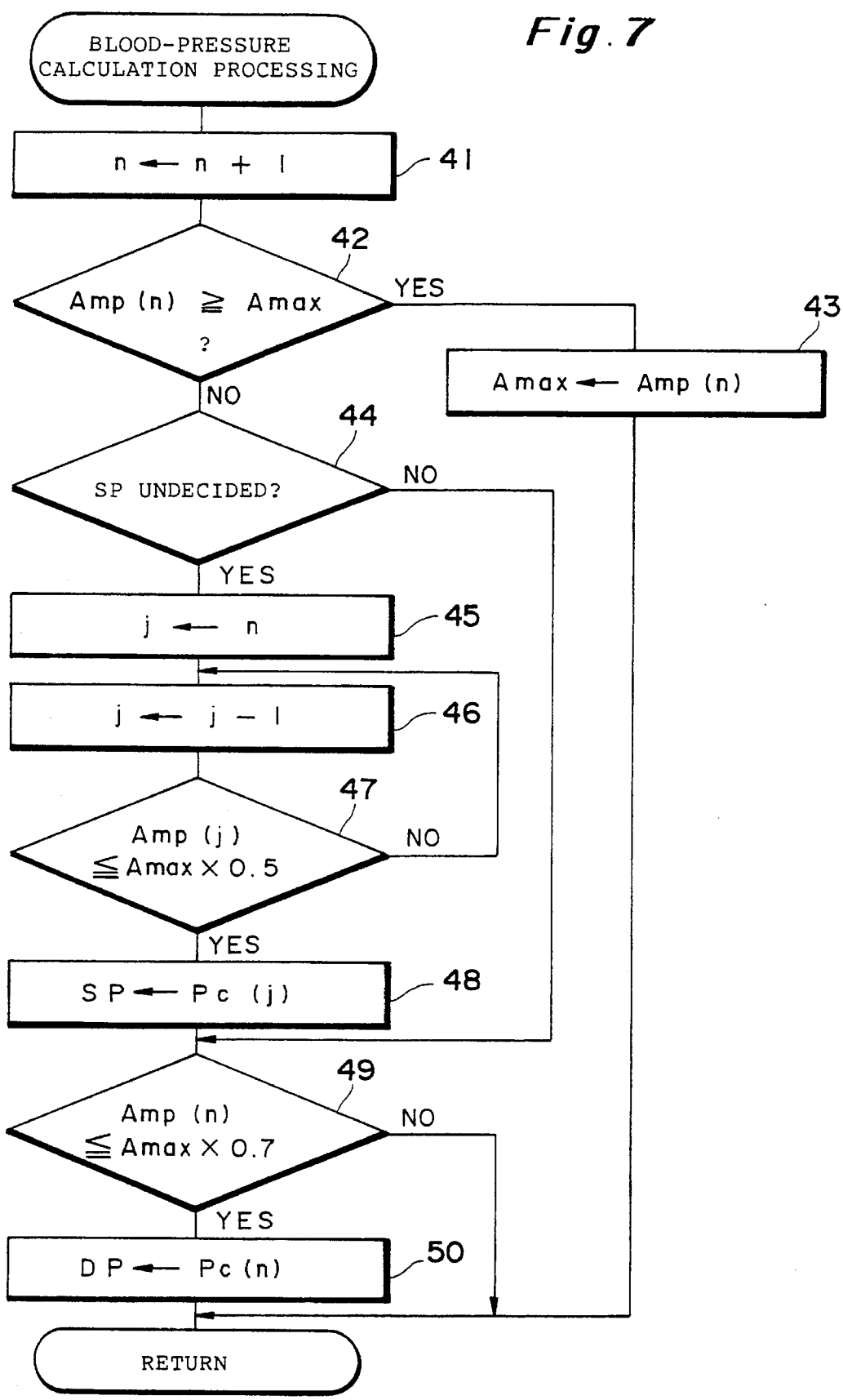
FIG. 7 is a flowchart showing the details of processing for calculating blood pressure.

FIG. 7 illustrates the details of processing (step 25 in FIG. 2) for calculating blood pressure.

In processing for calculating blood pressure, use is made of the table, shown in FIG. 3, to which data is added whenever a pulse wave is detected in the course of depressurization. The CPU 8 is provided with a counter for counting the number n of the pulse wave and registers (or storage areas of the memory) for storing respectively the systolic pressure SP and diastolic pressure DP that have been determined. These registers are initialized to 0 in advance of processing for measuring blood pressure.

First, detection of the maximum pulse-wave amplitude (which corresponds to Amaxd in FIG. 5) in the depressurization process is carried out. To this end, a register (or a storage area of the memory) for storing the maximum value Amax of pulse-wave amplitude at each processing instant is prepared (the initial value of Amax is 0). Whenever a transition is made to the processing routine for calculating blood pressure, the value of the count in the pulse-wave number counter is incremented (step 41), the amplitude Amp(n) of the pulse wave of the number designated by the count in the pulse-wave number counter (this amplitude is that calculated at the immediately preceding steps 18, 19) is compared with the maximum value Amax of the pulse-wave amplitude up to this time stored in the register (step 42), and the maximum value Amax is updated (step 43) by Amp(n) if Amp(n) is greater than Amax.

When the detected pulse-wave amplitude Amp(n) falls below the stored maximum value Amax of the pulse-wave for the first time, it is judged that the peak point on the envelope of the pulse-wave amplitude has been traversed (NO at step 42). If the content of the register for storing the systolic pressure (maximum blood pressure) SP is 0, then this means that the systolic pressure SP has not yet been determined and, hence, the program proceeds to processing for determining systolic pressure SP (YES at step 44).

In order to decide the systolic pressure SP, the data obtained thus far in the table shown in FIG. 3 is traced backwards in successive fashion to find the pulse-wave amplitude whose size is 50% of the maximum pulse-wave amplitude Amax detected. To this end, the pulse-wave number n in the counter at this time is set in an auxiliary counter (let j be the count in the auxiliary counter) (step 45) and the value j of the count in the auxiliary counter is decremented one count at a time (step 46). While the auxiliary counter is being decremented, the pulse-wave amplitude Amp (j) of the pulse-wave number designated in the table (FIG. 3) by this value j of the count is compared with Amax×0.5 (step 47). When the pulse-wave amplitude Amp(j) has become equal to or less than Amax×0.5 (YES at step 47), the cuff pressure Pc(j) stored in correlation with the pulse-wave amplitude Amp ( j ) is adopted as the systolic pressure (maximum blood pressure) SP (step 48).

In a case where systolic pressure has already been decided (NO at step 44), the program proceeds to processing for calculating diastolic pressure (minimum blood pressure) DP. A check is performed to determine whether the pulse-wave amplitude Amp(n) designated by the count n in the pulse-wave number counter is 70% of the maximum pulse-wave amplitude Amax (step 49). When the pulse-wave amplitude Amp(n) is equal to or less than Amax×0.7, the cuff pressure Pc(n) stored in correlation with this pulse-wave amplitude Amp(n) is adopted as the diastolic pressure (minimum blood pressure) DP (step 50).

Industrial Applicability

Electronic sphygmomanometers are manufactured and sold in the medical equipment industry and find use in medical facilities as well as in the home.

What is claimed is:

1. An electronic sphygmomanometer having pressurizing means for pressurizing a cuff to a prescribed target pressure value, depressurizing means for gradually depressurizing the cuff after the cuff is pressurized to the prescribed target pressure value by the pressurizing means, pressure detecting means for detecting fluid pressure within the cuff, pulse-wave extracting means for extracting, from a cuff pressure signal obtained from the pressure detecting means, a heartbeat-synchronized pulse-wave component signal superimposed upon the cuff pressure signal, pulse-wave amplitude detecting means for detecting amplitude of a pulse wave extracted by the pulse-wave extracting means for every heartbeat, and blood-pressure determining means for determining a value of blood pressure based upon an amplitude signal from the pulse-wave amplitude detecting means and a pressure signal from the pressure detecting means in the course of cuff depressurization by the depressurizing means, said electronic sphygmomanometer comprising:

maximum pulse-wave amplitude detecting means for detecting a maximum value of pulse-wave amplitudes obtained from the pulse-wave amplitude detecting means in the course of cuff pressurization by the pressurizing means;

threshold-value calculating means for calculating a threshold value based upon the maximum value of pulse-wave amplitude detected by said maximum pulse-wave amplitude detecting means; and cuff pressurization-inadequacy judging means for comparing (i) an early-occurring pulse-wave amplitude obtained from the pulse-wave amplitude detecting means at a time early in the course of cuff depressurization by the depressurizing means with (ii) the threshold value calculated by said threshold-value calculating means, and for judging that cuff pressurization is inadequate if the early-occurring pulse-wave amplitude is greater than the threshold value.

2. An electronic sphygmomanometer according to claim 1, wherein the threshold value is calculated to be substantially equal to a pulse-wave amplitude corresponding to systolic pressure determined in the course of depressurization.

3. An electronic sphygmomanometer according to claim 1, further comprising:

cuff repressurizing control means, operative when cuff pressurization is judged to be inadequate by said cuff pressurization-inadequacy judging means, for setting a new target pressure value greater than the prescribed target pressure value, for suspending depressurization of the cuff by the depressurizing means, and for controlling the pressurizing means to re-pressurize the cuff to the new target pressure value.

4. In an electronic sphygmomanometer having a pressurizing pump for pressurizing a cuff, a control valve for reducing pressure within the cuff, a pressure sensor for detecting fluid pressure within the cuff, and control circuit means for pressurizing the cuff to a prescribed target pressure value by the pressurizing pump, then gradually depressurizing the cuff by opening the control valve, detecting, for every heartbeat, the amplitude of a heartbeat pulse-wave component, which is synchronized to the heartbeat, superimposed upon the cuff pressure detected by the pressure sensor in the course of depressurization, and determining a value of blood pressure based upon cuff pressure and pulse-wave amplitude detected in the course of cuff depressurization, a method for controlling operation of the sphygmomanometer comprising:

detecting (i) the amplitude of the pulse-wave component of every heartbeat, and (ii) a maximum value of the detected pulse-wave amplitudes in the course of pressurizing the cuff to the prescribed target pressure value;

calculating a threshold value based upon the maximum value of pulse-wave amplitude detected; and comparing (i) an early-occurring pulse-wave amplitude obtained at a time early in the course of cuff depressurization, which begins after the cuff is pressurized to the prescribed target pressure value, with (ii) the threshold value, and judging that cuff pressurization is inadequate if the early-occurring pulse-wave amplitude is greater than the threshold value.

5. A method of controlling operation of an electronic sphygmomanometer according to claim 4, wherein the early-occurring pulse-wave amplitude compared with the threshold value is an amplitude of a pulse wave of a first heartbeat obtained in the course of cuff depressurization.

6. A method of controlling operation of an electronic sphygmomanometer according to claim 4, wherein the threshold value is substantially equivalent to a pulse-wave amplitude corresponding to systolic pressure determined in the course of depressurization.

7. A method of controlling operation of an electronic sphygmomanometer according to claim 4, wherein, when cuff pressurization is determined to be inadequate, said method further comprises (i) setting a new target pressurization value greater than the prescribed target pressure value, (ii) suspending depressurization, and (iii) repressurizing the cuff to the new target pressurization value.

8. An electronic sphygmomanometer having pressurizing means for pressurizing a cuff to a prescribed target pressure value, depressurizing means for gradually depressurizing the cuff after the cuff is pressurized to the prescribed target pressure value by the pressurizing means, pressure detecting means for detecting fluid pressure within the cuff, pulse-wave detecting means for detecting a heartbeat-synchronized pulse-wave component signal, pulse-wave amplitude detecting means for detecting amplitude of a pulse wave extracted by the pulse-wave detecting means for every heartbeat, and blood-pressure determining means for determining a value of blood pressure based upon an amplitude signal from the pulse-wave amplitude detecting means and a pressure signal from the pressure detecting means in a course of cuff depressurization by the depressurizing means, said electronic sphygmomanometer comprising:

maximum pulse-wave amplitude detecting means for detecting a maximum value of pulse-wave amplitudes obtained from the pulse-wave amplitude detecting means in the course of cuff pressurization by the pressurizing means;

threshold-value calculating means for calculating a threshold value based upon the maximum value of pulse-wave amplitude detected by said maximum pulse-wave amplitude detecting means; and cuff pressurization-inadequacy judging means for comparing (i) an early-occurring pulse-wave amplitude obtained from the pulse-wave amplitude detecting means at a time early in the course of cuff depressurization by the depressurizing means with (ii) the threshold value calculated by said threshold-value calculating means, and for judging that cuff pressurization is inadequate if the early-occurring pulse-wave amplitude is greater than the threshold value.

9. In an electronic sphygmomanometer having a pressurizing pump for pressurizing a cuff, a control valve for reducing pressure within the cuff, a pressure sensor for detecting fluid pressure within the cuff, a pulse-wave detecting means for detecting a heartbeat-synchronized pulse-wave component, and control circuit means for pressurizing the cuff to a prescribed target pressure value by the pressurizing pump, then gradually depressurizing the cuff by opening the control valve, detecting, for every heartbeat, the amplitude of a heartbeat pulse-wave component in a course of depressurization, and determining a value of blood pressure based upon cuff pressure and pulse-wave amplitude detected in the course of cuff depressurization, a method for controlling operation of the sphygmomanometer comprising:

detecting (i) the amplitude of the pulse-wave component of every heartbeat, and (ii) a maximum value of the detected pulse-wave amplitudes in the course of pressurizing the cuff to the prescribed target pressure value;

calculating a threshold value based upon the maximum value of pulse-wave amplitude detected; and comparing (i) an early-occurring pulse-wave amplitude obtained at a time early in the course of cuff depressurization, which begins after the cuff is pressurized to the prescribed target pressure value, with (ii) the threshold value, and judging that cuff pressurization is inadequate if the early-occurring pulse-wave amplitude is greater than the threshold value.

* * * * *